United States Patent [19]

Evers

[11] Patent Number: 5,300,358
[45] Date of Patent: Apr. 5, 1994

[54] DEGRADABLE ABSORBANT STRUCTURES

[75] Inventor: Glenn R. Evers, Wilmington, Del.

[73] Assignee: E. I. Du Pont de Nemours and Co., Wilmington, Del.

[21] Appl. No.: 956,325

[22] Filed: Nov. 24, 1992

[51] Int. Cl.$^5$ .................... A61F 13/46; A61F 13/52; B32B 5/26; B32B 33/00

[52] U.S. Cl. .................................. 428/286; 428/422; 428/913; 604/364; 604/366; 604/372; 604/376; 604/382

[58] Field of Search ............... 604/364, 366, 372, 376, 604/382; 428/286, 422, 913

[56] References Cited

U.S. PATENT DOCUMENTS

| | | | |
|---|---|---|---|
| 2,999,788 | 9/1961 | Morgan | 162/146 |
| 3,683,919 | 8/1972 | Ells | 604/364 |
| 3,844,987 | 10/1974 | Clendinning | 47/66 |
| 3,923,715 | 12/1975 | Dettre et al. | 524/199 |
| 4,057,537 | 11/1977 | Sinclair | 528/354 |
| 4,458,042 | 7/1984 | Espy | 524/14 |
| 4,463,043 | 7/1984 | Reeves et al. | 428/68 |
| 4,687,478 | 8/1989 | Van Tilburg | 604/387 |
| 4,742,140 | 5/1988 | Greenwood et al. | 526/245 |
| 4,900,299 | 2/1990 | Webb | 604/11 |
| 5,015,245 | 5/1991 | Noda | 604/367 |
| 5,026,589 | 6/1991 | Schechtman | 428/138 |

FOREIGN PATENT DOCUMENTS 01521 2/1990 PCT Int'l Appl. .

OTHER PUBLICATIONS

E. Matijevic & F. Eirich, Ed., "Wettability and Contact Angle," Surface & Colloid Science (Interscience, N.Y. N.Y. 1969) p. 85.

Fox & Sisman, "The Spreading of Liquids on Low Energy Surfaces, I. Polytetrafluoroethylene," J. Colloidal Sciences, pp. 515-531.

Ellison & Zisman, "Wettability Studies of Nylon Polyethylene Terephthalate and Polystyrene," Journal of Physical Chem. 58, pp. 503-506 (1954).

Primary Examiner—James C. Cannon

[57] ABSTRACT

Compostible and flushable absorbent structures for sanitary uses for the absorption of body fluids comprising an absorbent degradable fibrous core and a backsheet that is cold-water soluble but water impermeable.

23 Claims, 1 Drawing Sheet

DEGRADABLE ABSORBANT STRUCTURES

BACKGROUND OF THE INVENTION

1. Field of the Invention

This invention relates to compostible non-rigid absorbent structures comprising an absorbent degradable fibrous core and a backsheet that is cold water soluble and contains on both sides of the backsheet a discontinuous layer of aqueous-repellent material. A preferred species can be disposed of by toilet flushing.

2. Description of Related Art:

Landfill solid waste disposal sites are rapidly filling to capacity. A significant contribution to the landfills are absorbent batting materials, particularly diapers and feminine hygiene products. These products typically contain non-biodegradable polyolefins that do not degrade rapidly when buried.

Most municipal and septic sewage systems process solid waste by biodegradation. Therefore, the problem of overloading landfill capacity could be helped significantly if batting products were flushable, biodegradable and/or hydrolyzable and so could readily be recycled into the environment via a sewage system.

Noda U.S. Pat. No. 5,015,245 discloses disposable sanitary articles comprising a topsheet, a backsheet, and an absorbent core, wherein the backsheet is paper treated with a specific type of latex for improved wet strength. Any conventional core material can be used.

Scheckman U.S. Pat. No. 5,026,589 discloses disposable sanitary garments comprising top and/or back sheets prepared from polymers based on dioxanone.

Ells U.S. Pat. No. 3,683,919 discloses a flushable sanitary napkin comprising an absorbable cellulosic fibrous core, between a topsheet and a backsheet that can be torn apart and separated from the core for flushing. The top and backsheets may be biodegradable or not, but can be processed through municipal and septic sewer systems. This product has the disadvantage that before flushing the top and backsheets must be torn apart to expose the cellulose core to the sewage system.

Morgan U.S. Pat. No. 2,999,788 discloses the manufacture of highly branched discontinuous fibrils by a spurting technique.

Clendening U.S. Pat. No. 3,844,987 discloses relatively non-absorbable rigid seed germination containers made from naturally occurring biodegradable material such as wood pulp bonded by a biodegradable thermoplastic oxyalkanoyl polymer to give it strength.

Sinclair U.S. Pat. No. 4,057,537 discloses laminates made from a polyhydroxic acid (PHA), copolymer fibrous matrix which is consolidated into a rigid, non-porous laminated structure by flowing molten polymer through the fibrous material and curing it while in a mold or hydraulic press. Synthetic or natural fibers such as cellulose fibers are disclosed as the matrix.

Battelle Patent Application WO 90/01521 discloses non-porous rigid laminates made from a fibrous mat consolidated by flowing molten PHA polymer through the fibrous material and curing the polymer in a mold or hydraulic press. Fibers can include cellulose derived from wood.

Copending and commonly assigned U.S. patent application Ser. No. 07/718,938 filed Jun. 21, 1991, and now abandoned, disclose paper products comprising cellulosic fiber blended with PHA fibrous materials. The blend is heated to bond, giving a strong, liquid absorbing hydrophilic batting.

Copending and commonly assigned U.S. patent application Ser. No. 07/743,850 filed Aug. 12, 1991, discloses PHA shaped articles protected against premature degradation by one or more surfaces being coated with a discontinuous layer of hydrophobic and/or oleophobic material that will repel degrading liquids.

Totally degradable polymers are being used more frequently in health care products. Webb U.S. Pat. No. 4,900,299 discloses a biodegradable tampon applicator with a molded, hollow cylindrical body of a moldable degradable poly-3-hydroxybutyric acid composition.

Espy U.S. Pat. No. 4,458,042 describes improved absorbent materials formed by blending wood fluff pulp and spurted polyolefin pulp which has been treated with a wetting agent substance, and then heating the blend at a temperature for a time sufficient to consolidate the treated spurted polyolefin pulp.

Cellulosic products bonded with polyolefins do not degrade as rapidly, or completely, as cellulosic products bonded with poly(hydroxy acid) (PHA) polymers. Carl Lehrburger, author of a reusable diaper industry funded report titled "Diapers In The Waste Stream", suggests a design change. "The only biodegradable diaper may be the two piece diaper with a reusable cover and a flushable pad", his report says "However, this is not commercially available or feasible at this time." (Nonwovens Industry, October 1989, Pg. 24).

SUMMARY OF THE INVENTION

Compostible and flushable non-rigid, highly absorbent structures, particularly for sanitary uses for the absorption of body fluids, comprising an absorbent degradable fibrous core and a backsheet that is cold-water soluble but water repellent on the inner and outer sides.

DESCRIPTION OF THE PREFERRED EMBODIMENTS

Figure 1:
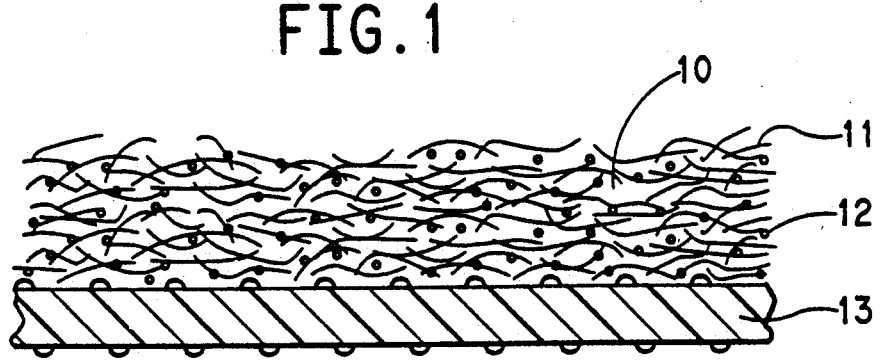
FIG. 1 shows the broad concept of the absorbent structure of the present invention wherein 10 is the core comprising 11 fibrous material and optionally 12 super absorbent polymer and the backsheet 13 coated on both external surfaces with discontinuous coextensive layers of water repellent material 14.
Figure 2:
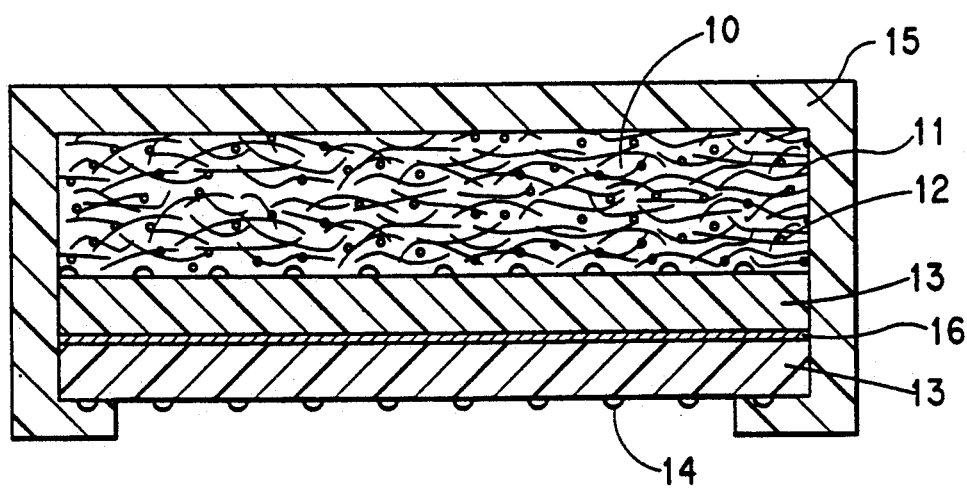
FIG. 2 shows a preferred embodiment additionally comprising topsheet 15 which may overlap around the core and be attached to the outer surface of the backsheet 13 as shown, and a layer of "water dissolvable" paper 16 between two layers of water dissolvable backsheet material.

The present invention relates to compostible absorbent non-rigid structures ideally suited for sanitary uses, particularly for the absorption of aqueous body fluids. The structures comprise a highly porous, absorbent, degradable fibrous core and a backsheet of specific design attached to the core. In the preferred embodiment, the structures also comprise a topsheet that is water-permeable and degradable. These structures are substantially completely degradable and can be disposed of by composting. Many of the structures can be disposed of by flushing into a sewage system. Environmentally, these structure readily degrade primarily to benign water and carbon-dioxide.

The term "degradable" as used herein means that the structure is able to breakdown under typical environmental and/or composting waste treatment conditions (e.g., via hydrolysis or other chemically assisted degradation and/or biodegradability) to gas and/or aqueous products in concentrations generally harmless to the environment. The degradation rate is consistent with the intended use of the structure, i.e., the structure does not degrade significantly under normal storage or use conditions but will degrade in a reasonable time under the conditions of disposal. The term "biodegradable" defines a process whereby microorganisms such as bacteria, fungi, yeasts, etc., and/or their enzymes consume part or all of the article so that its original form substantially disappears.

Minor quantities of substantially harmless inert particles (e.g., pigments and repellent materials), that do not "degrade", as defined above, can be present in the "degradable" structures of this invention. Thus, the structures of the present invention are substantially, totally degradably by:

(1) aqueous exposure (hydrolysis);
(2) biodegradability, with or without prior treatment, under environmental or waste disposal conditions. Both solids and solutions of chemicals, such as polyvinyl alcohol, dissolved out of the structures of the present invention, may biodegrade and/or;
(3) chemically degradable via simple environment-/compost waste treatment conditions or by recycle or sewage chemical treatment.

The terms "topsheet", "backsheet", and "core", as used herein, have the meaning conventional in the diaper art. See Noda U.S. Pat. No. 5,015,245. Specifically the topsheet is the layer adjacent to the human skin; the backsheet is the layer remote from the skin; and the core is the batting material interposed between the topsheet and the backsheet. Of course the structure may contain more than three layers, but these are the significant components of the sanitary absorbent structures of the present invention. In products that in use do not come in contact with human skin, the terms simply refer to sheets attached to the core structure, the backsheet being on one surface of the core and the topsheet, if present, being on the opposite surface of the core.

The core comprises any non-rigid highly absorbent degradable material. By highly absorbant is meant that the material is highly porous and hydrophilic. For purposes of this invention, the absorbent core material must be porous at least to the extent of 70%, and preferably 90%, voids (air) space.

Preferably the core material comprises a major proportion of cellulosic fibrous material, from 50-100% of fibrous material. It may be an oxidized cellulose as described in Scheckman U.S. Pat. No. 5,026,589. An ideal cellulosic fibrous material is wood fluff pulp because it has high bulk, and excellent absorbency and softness. Fluff pulp can be used alone or blended with other cellulosic or non-cellulosic fibrous material.

The grades of wood fluff pulp and the methods of its preparation are known to those skilled in the art. Wood pulp can be obtained from well known chemical processes such as the kraft and the sulfite processes. For these processes, the best starting material is prepared from long fiber, coniferous wood species, such as pine, Douglas fir, blue fir, spruce and hemlock. Wood pulp also can be obtained from mechanical processes, such as ground wood, refiner mechanical, thermomechanical, chemimechanical, and chemithermomechanical pulp processes. Details of the production and use of wood pulp are well known to one skilled in the art.

In addition to cellulosic pulp, other types of fibrous core materials can comprise from 0-100% of the core fibrous material. The fibrids of U.S. Pat. No. 2,999,798 disclose PHA pulps spurted or fibrillated that are excellent core absorbent materials. These are very fine highly branched, discontinuous fibrils made from thermoplastic PHA polymers. Their visual appearance and dimensions can closely resemble those of wood pulps. Fibrillated PHA pulps have a large surface area (about 3-50 $m^2/g$), low densities (about 0.2 g/cc as measured by mercury poro-simetry for spurted polylactide and about 0.4 g/cc for spurted polyglycolide, an average length of about 1 mm and an average diameter of about 5-40 microns.).

When used, the amount of fibrillated PHA pulp in the blend is up to 100%, and preferably from about 3 to about 30%, based on the total weight of the fibrous material. The optimal composition for a particular blend will depend on the fibrillated PHA pulp chosen and the properties desired in the final absorbent material. Generally, it has been found that as the percentage of fibrillated PHA pulp increases, the strength of the absorbent material also increases.

Another highly effective PHA core material is cut staple fibers, preferably less than 3 denier and less than 1 inch in length. These staple fibers can be made by melt-spinning PHA, drawing the continuous filament to the desired denier, and cutting to the desired staple length.

One or more absorbing agent desirably is also included in the core to absorb and hold a large quantity of aqueous body fluid. The absorbing agent must be degradable and non-toxic to the disposal system and the environment so that it does not kill the microorganisms in sewage disposal systems or leave a toxic residue. Many excellent absorbing agents are known, often referred to as "superabsorbent polymers", that can absorb 100-1500 times their weight in water. See Stanford Research Institute report 194 "Superabsorbent Polymers", November 1990. When used, the absorbing agent makes up to 10 to 50% by weight of the core material. See Scheckman U.S. Pat. No. 5,026,589 for details on absorbents and their use.

The fibrous core material may be treated with a wetting agent substance. A wetting agent substance is a surface-active agent which reduces the surface tension of water, as water comes into contact with the treated material, thus causing the water to more readily penetrate throughout the fibrous batting core thereby increasing its absorbency.

The wetting agent substance treatment is done in a variety of ways which are known in the art. A preferred method is to spurt PHA pulp directly into an aqueous solution containing the wetting agent substance, under which conditions the wetting agent substance is absorbed onto the surface of the fiber. Other methods include spraying a solution of the wetting agent substance onto the fibrous material before or after blending, or adding the wetting agent substance to a fibrous slurry during the blending process. Other methods will be apparent to those skilled in the art.

The treatment is such that from about 0.05 to about 3%, preferably from about 0.1 to about 1%, based on the weight of the fibrous material, of the wetting agent substance is retained.

In one embodiment the wood pulp and the pulped PHA pulp are blended. Any of the known blending methods, such blending by codepositing during the preparation of a pulp sheet by conventional paper-making procedures, or by conventional dry blending methods.

After blending, the fibrillated PHA and wood pulps may be fluffed and formed into a fluff pad by conventional methods such as hammermilling or air forming.

In other embodiments, the PHA and wood pulps may be fluffed prior to blending. The order of fluffing and blending is not critical.

If the fibrous core contains PHA and greater integrity or stiffness is desired, it may be consolidated by heating at a temperature and for a time sufficient to fuse the PHA. Slight pressure during heating may be desirable. It has been found that consolidation not only increases the strength but improves the absorbency of the core. Fusion will occur by raising the temperature above the PHA's softening point. Representative methods to fuse the PHA include the use of heated calender rolls, infrared heaters and pull-through driers and the like. Exact conditions, which will be readily ascertained by one skilled in the art, must be determined for the specific blend being used. The time, which will be readily ascertained by one skilled in the art, generally ranges from 1 second to about 10 minutes. Where a cellulosic fibrous core of improved batting strength, but with ease of disintegration is desired, a batting core can be used that comprises fibrous cellulosic and PHA bonded at contact points between cellulose and PHA fibers by heat softening (not liquid flow melting) the PHA.

For many uses, such as where a topsheet is not used, fusion and bonding particularly of the top side of the core opposite from the backsheet can give adequate structural stability to the core to eliminate the need for a topsheet, with the added advantage of improved degradability and flushability. The more highly fused top side of the core functions as a topsheet.

For many uses the structures of the present invention are flushable, that is can be directly discarded into a toilet and flushed. These flushable structures must be small enough or break down in the toilet water to small enough pieces to flush. Therefore, for larger flushable articles the core may be segmented into unconnected individual pieces of a flushable size, preferably having a minor cross section of not over 2 square inches, desirably not over 1 square inch. Desirably, the segmented core structure is designed to avoid channeling of the liquid through the core directly to the backsheet.

The backsheet is an impermeable sheet material that rapidly dissolves in cold water, and is thereby released from the core. This is particularly important where the structure is to be flushed, so that core segments are rapidly freed from the dissolved backsheet before flushing. The backsheet is strong enough for handling and flexible enough to fit body contours comfortably. Typical materials for the backsheet are polyvinyl alcohol (PVA), starches, rice paper, guar gum and the like.

The backsheet may be a single layer, but preferably it comprises several layers. An excellent backsheet comprises two sheets of PVA film, with a layer of highly absorbent paper in between made from carboxymethylcellulose and cellulose. The backsheet may be a continuous, water impermeable film. Alternatively for "breathing" the backsheet may be a porous sheet material such as a non-woven fabric. The repellent surface treatment prevents water penetration.

An essential feature of the structures of the present invention is that the highly water soluble, and optionally porous, backsheet has external surfaces, including edges that are hydrophobic and so repel both water and body fluids. To achieve this hydrophobic nature the soluble backsheet surface contains or is coated on all surface areas that are to be protected from water contact, normally both external surfaces and edges, with a repellent. The repellent is applied coextensively over the entire area to be protected, but must be discontinuous (i.e., perforate or porous in a micro sense) to allow wetting of the backsheet when the surface tension of the dissolving water is sufficiently decreased as described below and in copending and commonly assigned U.S. patent application Ser. No. 07/743,850, which is incorporated herein by reference.

The repellent may be incorporated into the backsheet so long as it is exposed and comprises part of the surface; or the repellent may be applied as a surface layer by any technique that results in a discontinuous layer with adequate physical and/or chemical bonding to the surface of the degradable substrate material. The discontinuous repellent material coating or layer extends generally over the entire inside and outside area of the backsheet. The repellent surface must be discontinuous and normally the repellent material comprises discrete particles or a perforated layer or sheet. Alternatively, the repellent material can be in the form of a porous surface layer such as a woven or non-woven fabric material, a lattice, elongated particles, filaments, etc. Further, the repellent material may comprise coated particles and/or fibers (e.g., a fiber may be rendered repellent by being coated with a repellent material).

The repellent surface comprises a hydrophobic material that has an adequately low critical surface tension to repel the particular assaulting liquid (water and body fluid) to which the article will be exposed, and sufficiently discontinuous to eventually permit the adjacent degradable backsheet to dissolve or degrade. For purposes of this invention, a hydrophobic material comprises a material that will prevent wetting of the substrate (backsheet) by an aqueous assault liquid. The repellent surface discussed above may also comprise a material that is both hydrophobic and oleophobic which will prevent wetting of the substrate by both aqueous and organic assault liquids.

The repellent surface may comprise one or more of the following repellent materials: paraffin, waxes, fatty acids, bee's wax, silicones, fluorochemicals, alkylketene dimers, and the like.

An excellent repellent surface material comprises a particulate perfluoroalkyl material in a non-aqueous solvent (e.g., "TEFLON" SBB which is manufactured by E. I. du Pont de Nemours and Company). These perfluoroalkyl materials may be in combination with other non-fluorinated polymers, such as a non-fluorinated vinyl polymer and a perfluoroalkyl ester of a carboxylic acid (e.g., refer to the disclosure of Dettre et al. U.S. Pat. No. 3,923,715 which is hereby incorporated by reference). A suitable repellent material may also comprise interpolymers of a perfluoroalkylacrylate (e.g., "ZONYL" 7040 which is manufactured by E. I. du Pont de Nemours and Company) and other non-fluorinated polymers (e.g., refer to the disclosure of Greenwood et al., U.S. Pat. No. 4,742,140 which is hereby incorporated by reference).

As described more fully in the aforementioned pending U.S. patent application Ser. No. 07/743,850, the surface tension of the repellent material is vital to the products of the present invention. The repellent surface layer must have a surface tension from about 5 to 54 dynes per cm. and, for best results, normally not above about 30 dynes/cm. The surface tension of the repellent material enables the repellent material to protect the substrate from assaulting liquids.

The advancing contact angle measured between the repellent surface layer and the assaulting liquid must be at least about 70°. For further information on the advancing contact angle, see "Wettability and Contact Angle", Surface and Colloid Science, Vol. 2, E. Matijevic and F. Eirich, Ed., (Interscience, New York, N.Y. 1969), pg. 85; "The Spreading of Liquids on Low Energy Surfaces. I. Polytetrafluoro-ethylene", Fox and Zisman, p. 515-531, J. Collidal Sciences; and "Wettability Studies of Nylon, Polyethylene Terephthalate and Polystyrene", Ellison and Zisman, Journal of Physical Chemistry 58, p. 503-506 (1954). The disclosure of each of the above publications is hereby incorporated by reference.

The Matyevic et al. reference demonstrates a technique for calculating the advancing contact angle O by using the formula:

$$\cos O = 1 + m([1/v] - [c])$$

where
$m = -0.037$ cm./dynes
$[1/v]$ = the surface tension of the assaulting liquid, dynes/cm
repellent surface layer, dynes/cm.

An upper limit surface tension for the repellent surface layer of about 54 dynes/cm. is suitable for aqueous liquids.

For example, water has a surface tension of 72 dynes/cm; a repellent surface of 13 dynes/cm will readily repel water.

For water repellency and protection from aqueous body fluids, many silicone materials have adequately low critical surface tensions for excellent repellency (e.g., water having a surface tension of 72 dynes/cm can readily be repelled by silicone or other hydrophobic materials with a surface tension of below about 24) dynes/cm).

In another aspect of the invention, a surfactant is used to increase the rate of water solubility of the backsheet of the present articles. For example, soluble degradable synthetic backsheet of a diaper of the invention may be coated with a fluorochemical repellent; after use, the repellent can be wetted with the assistance of a fluorosurfactant such as "ZONYL" FSO. The surfactant, put in the disposal water, reduces the surface tension of the repellent layer, which in turn permits the degradable backsheet to be dissolved rapidly in the cold water. Sufficient concentration of surfactant decreases the advancing contact angle to less than 70°.

In this embodiment of the invention, the fluorochemical repellent does not permit the backsheet to be wet by an assaulting liquid until the fluorochemical repellent is contacted with the surfactant. Therefore, for disposal of absorbent structures like diapers via the toilet, the toilet water dissolves the backsheet, the segments of the core break-up into flushable size pieces, and the top sheet is flushed to enter a degradable environment. To enhance the wetting and dissolving of the backsheet for flushable disposal, the toilet water contains the necessary small amount of a surfactant to decrease the advancing angle to less than 70°.

In another embodiment of the invention, the backsheet is exposed to an aqueous fluid and dissolved by disrupting the coextensiveness of the repellent surface layer. This technique is very applicable where the repellent coated backsheet has a means, such as a tear strip or string, that disrupts the continuity of the repellent coating thereby exposing uncoated backsheet edges to the aqueous fluid. Upon exposure to water after the tear strip is torn, the water degrades the backsheet via the edges. Rapid degradation occurs if the backsheet is multilayered, an inner layer of which wicks water rapidly such as highly absorbent paper.

In degradation, the degradable backsheet portion of the article in water solution is converted by hydrolysis and/or bacterial activity, possibly accompanied with photo and other chemical activity, into environmentally benign products (e.g., photo-oxidation, elevated temperature aqueous alkali treatment, etc.). The repellent surface material on the backsheet, present in a low percentage, along with any inert fillers and the like, may remain as powders after the backsheet is substantially completely degraded.

When present, the topsheet is a porous degradable sheet or film-like material that will allow the passage of body fluid to the core, and that will not degrade in use, but will degrade under the conditions of disposal. Woven fabric, gauze, netting and non-woven structures are normally used in the topsheet, comprising fibers filaments or fibrous degradable materials.

Preferably the topsheet and the core fibrous material comprise a synthetic polymeric degradable PHA polymeric material from the formula:
(i) (OCD'R"COOCR'R"CO)q
(ii) [O(CR'R")$_n$CO]p
(iii) (OCR'R"CR'R"OCR'R"CO)r
(iv) (OCR'R"CR'R"ZCR'R"CR'R"CO)s
(v) copolymers of (i)-(iv) with non-hydroxy acid comonomers wherein n is 2, 4 or 5; p, q, r and s are integers, the total of which may range from about 350 to 5,000; R' and R" comprise hydrogen, hydrocarbyl containing 1 to 12 carbon atoms, or substituted hydrocarbyl containing 1 to 12 carbon atoms; and z is O, S, NH or PH. In addition to the generally linear polymers disclosed above, many branched HA polymers are useful in the products of the invention. Suitable branched polymers have a central residue of a polyfunctional compound with amino and-/or hydroxyl groups, and attached to the amino and/or hydroxyl are branches or arms formed of polylactide, polyglycolide, polycaprolactone or mixtures thereof. Useful branched polymers and their manufacture are disclosed in copending and coassigned U.S. patent application Ser. No. 07/815,995, now U.S. Pat. No. 5,225,521, which is incorporated herein and made a part hereof.

Examples of suitable non-hydroxy acid co-monomers comprise those capable of condensation polymerization with lactide or lactic acid, e.g., lactones such as epsilon-caprolactone; beta-propiolactone; alpha, alphadimethyl-betapropiolactone; and dodecanolactone; lactams, other hydroxy acids such as glycolic acid; and amino acids.

A desirable PHA comprises polylactic acid, and/or polyglycolic acid, either as homopolymer or as copolymer containing over 50%, and normally over 70%, of lactide and/or glycolic units. For certain articles, the "L" isomer of lactide is desirable since L-lactide is naturally present in the human body and in certain foods such as milk.

When the structure is to be disposed of by toilet flushing, all solid material must be of flushable size. Whereas the backsheet dissolves in the toilet water as hereinbefore described, the topsheet must be sufficiently non- or slowly soluble to maintain its integrity during its intended use.

PHAs of varying degree of water resistance can be made. Including the proper quantity of a water stabilizing material in the PHA topsheet can give it adequate water insolubility for its intended use, but adequate solubility to disintegrate when placed in liquid water. Fine denier and large mesh topsheets dissolve more rapidly.

Alternatively, a segmented topsheet can be used to impart adequate structural stability to the fibrous core, segmented into sufficiently small pieces to flush and rapidly degrade by hydrolysis to prevent plugging of pipes. Such a segmented topsheet construction can be used for a flushable diaper.

EXAMPLE 1

A flushable disposable baby diaper insert pad is prepared as follows. The dimensions listed are for a diaper insert intended for use with a child in the 6–10 kilogram size range. These dimensions can be modified proportionately for different size children, or for adult incontinence briefs, according to standard practice.

A flushable backsheet is prepared as follows: A 2 ply cold water soluble, 0.025 inches per ply polyvinyl alcohol (PVA) retangular pouch having a width-at-center of 28.5 cm and a length of 50.2 cm is coated on both exterior surfaces with a blade coating of solvent based water repellent fluorochemical, Du Pont "TEFLON" SBB (0.77% solids), such that the final weight of fluoropolymer solid is 0.1 pounds/1000 square feet of PVA film. The exterior surfaces are heated with 80° C. hot air to remove the coating solvent. (1,1,1-trichloroethane).

A "water dissolving paper", whose primary composition is carboxymethyl cellulose (CMC) and cellulose is cut to a 28 cm width-at-center and a length of 49 cm. The "water dissolving paper", 60 g/m$^2$, 44 mils thickness, 60 FD is made by Custom Papers Group, Inc., James River Corp, Richmond, Va. The paper is lightly sprayed slightly with a mist of water on both sides so that the final weight percent of water is 0.5 weight percent on an oven dry paper basis. Inserted lengthwise in the PVA pouch along the seam is a Customs Papers CMC/cellulose FD tear string oriented parallel and adjacent to the inner seam of the pouch. The 60 FD paper is mist treated to improve adhesion of the inside untreated cold water-soluble polyvinyl alcohol film to the paper surface. Care must be taken during spraying of the water so as to not swell the paper. The mist treated 60 FD paper is inserted into the cold-water soluble PVA pouch and heat sealed between two nonstick polyimidine film heating surfaces at 110° C. for 15 seconds.

The resulting composite pouch forms a backsheet, which when laid on a water surface, does not dissolve or disintegrate. Upon pulling the string out, thus ripping open the seam, the coextensiveness of the repellent layer is disrupted. Water wicks rapidly through the side opening into the 60 FD "water dissolving paper". As this water wicks through the 60 FD paper, the paper expands and exposes the inner, untreated cold-water-soluble PVA surface to the dissolving action of the water. Within minutes, the cold-water-soluble PVA film completely dissolves leaving behind fine particulate fluorochemical residue and dispersed cellulose.

An absorbent core is made containing three segments of oxidized cellulose batting (12–24% carboxyl). Each segment is 8.4 mm thick after calandering to a void content of about 80%, 9.5 cm in width and 44.0 cm in length. The three sements are placed side-by-side parellel to form a core of 8.4 cm×9.5 cm×44.0 cm.

A topsheet is prepared containing 3 layers of nonwoven polylactic acid fiber scrim sheets, each of 10 cm width and 50 cm long. These are placed side-by-side to form a topsheet 10 cm×50 cm.

A flushable diaper insert is prepared by glueing the backsheet and the topsheet on opposite surfaces of the segmented core using water soluble glue.

Upon disposal into a toilet containing a wetting agent, the backsheet dissolves and the segmented core and topsheets separate into flushable segments.

EXAMPLE II

A lightweight pantiliner suitable for use between menstrual periods is prepared by making an oxidized cellulose core of about 85% porosity (surface area 117 cm$^2$; SSK air felt 3.0 g) containing 1.0 g of absorbent gelling material particles (commercial polyacrylate; Nippon Shokubai);

The pad is interposed between a porous formed-film topsheet of polylactide according to U.S. Pat. No. 4,463,043; and a layered backsheet of treated film made by the technique described in Example 1 above, except that the dimensions conform to a pantiliner size, and the cold water soluble PVA film is 2 mils thick/ply and the "water dissolving paper" is 26 mils thick, 30 g/m$^2$, 30 FD made by Custom Papers Group Inc., Richmond, Va. Upon pulling out the backsheet string, the pantiliner can be flushed down a toilet, desirably containing a wetting agent.

EXAMPLE III

A catamenial product in the form of a sanitary napkin having two flaps extending outward from its absorbent core is prepared using a core made in accordance with Example II (surface area 117 cm$^2$; 8.5 g SSK air felt), per the design of U.S. Pat. No. 4,687,478. The backsheet comprises a treated film made by the techniques described in Example 1 above, except the dimensions conform to a catamenial product and the cold water soluble PVA film is 2 mils thick/ply and the "water dissolving paper" is 26 mils thick, 30 g/m$^2$, 30 FD made by Customs Papers Group Inc., Richmond, Va. The topsheet comprises a nonwoven scrim of polylactide fibers.

The product is totally degradable.

EXAMPLE IV

The sanitary napkin of Example III is modified by replacing the topsheet with a porous nonglossy film made in accordance with the disclosure in U.S. Pat. No. 4,687,478 said film being prepared from a polylactide 90/10 L, D polymer. This is a completely degradable product.

EXAMPLE V

A diaper insert is prepared by making a backsheet in accordance with the process of Example I, except that the backsheet external surfaces are not coated with a repellent. Instead, 2.5 mil long 1.5 denier polylactide staple filaments are scattered thoroughly over the entire surfaces of the backsheet, mist sprayed with water, and immediately dried against hot plate surfaces at 130° for 15 seconds to bond the fibers to the core surface. The average pore diameter of the pores between the fibers is less than 100 microns. The polylactide staple filament surface is sprayed with "TEFLON" SSB repellent at a rate of 0.1 pounds of repellent polymer per 100 square feet of surface area. In all other respects, the process of Example I is followed.

The product so prepared is a flushable, totally degradable product.

What is claimed:

1. A structure absorbent to aqueous fluids comprising a non-rigid core and a backsheet, said core comprising an absorbent, degradable fibrous material; and said backsheet comprising sheet material that is cold-water soluble, which backsheet has a external discontinuous repellent surface; said surface comprising a hydrophobic material that;

(i) is substantially discontinuous on the surface of the backsheet, said material covering at least about 80% of the total backsheet surface area that will be contacted by said fluids; and (ii) has a critical surface tension less than about 54 dynes/cm and sufficiently lower than the surface tension of said fluids to give an advancing contact angle between the surface layer and said fluid of at least 70°, thereby preventing said fluid from physically contacting the backsheet.

2. The structure of claim 1 comprising a porous degradable topsheet.

3. The structure of claim 2 wherein said topsheet comprises polyhydroxyacid.

4. The structure of claim 1 wherein said core fibrous material is selected from the group consisting of cellulosic, polyhydroxyacid materials and blends thereof.

5. The structure of claim 1 wherein the fibrous material of said core is bonded together at least on the side opposite the backsheet.

6. The structure of claim 1 wherein said core also contains a non-toxic super-absorbent material.

7. The structure of claim 4 wherein said core comprises fibrillated PHA.

8. The structure of claim 4 wherein said core comprises fluffed cellulosic fibrous material.

9. The structure of claim 6 wherein said super-absorbent material comprises 10 to 50% be weight the core.

10. The structure of claim 6 wherein said core has at least 70% void space.

11. The structure of claim 1 wherein said core is segmented into discrete units of a size for flushability.

12. The structure of claim 1 wherein said core is adhered to said backsheet by an adhesive.

13. The structure of claim 1 wherein said backsheet also comprises materials selected from the group consisting of fillers and fibrous materials.

14. The structure of claim 2 wherein said topsheet also comprises materials selected from the group consisting of fillers and fibrous materials.

15. The structure of claim 1 wherein said backsheet comprises cold-water soluble polyvinyl alcohol.

16. The structure of claim 1 wherein said discontinuous repellent surface comprises a perfluoroalkyl compound.

17. The structure of claim 1 wherein said backsheet comprises two layers of film with water absorbent paper between the two layers, said paper being non-contactable by fluid during usage.

18. The structure of claim 17 wherein said paper is a dispersible carboxymethylcellulose/cellulose paper.

19. The structure of claim 17 wherein said paper can be rendered directly contactable at least in part by fluid.

20. The structure of claim 1 wherein said core contains a wetting agent.

21. The structure of claim 1 selected from the group consisting of diapers, sanitary napkins, incontinent garments and pantyliners.

22. The structure of claim 1 comprising means to disrupt said repellent surface thereby rendering exposed uncoated backsheet.

23. The method of degrading a structure of claim 1 comprising exposing said structure to an aqueous medium containing surfactant in an amount sufficient to decrease said advancing angle to less than 70°.

* * * * *